US00PP36538P2

(12) United States Plant Patent
Warren

(10) Patent No.: US PP36,538 P2
(45) Date of Patent: Mar. 11, 2025

(54) RED MAPLE TREE NAMED 'WW Warren'

(50) Latin Name: *Acer rubrum*
Varietal Denomination: WW Warren

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 18/664,176

(22) Filed: May 14, 2024

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224
See application file for complete search history.

(56) References Cited

PUBLICATIONS https://www.fast-growing-trees.com/products/red-sentinel-maple-tree (retrieved on line Sep. 19, 2024)(Year: 2024).*

* cited by examiner

*Primary Examiner* — Susan McCormick Ewoldt
*Assistant Examiner* — Zachariah Allan Kay
(74) *Attorney, Agent, or Firm* — Klarquist Sparkman, LLP

(57) ABSTRACT

A new variety of red maple with a unique combination of characteristics, combining a fast growth rate tightly fastigiate branching habit. an extremely narrow to columnar form, small leaves with long acuminate tips that produce a delicate appearance, and bright red fall color.

7 Drawing Sheets

Latin name of the genus and species of the plant claimed: *Acer rubrum.*

Variety denomination: 'WW Warren'.

BACKGROUND

A selection program of *Acer rubrum* trees began in 1989. Selected seed sources and hybridization were used to develop improved cultivars, including an improved columnar form. A seed source collected in 1995 produced a cultivar that was named 'JFS-KW78' (U.S. Plant Pat. No. 25,301). During the pre-patent evaluation process of 'JFS-KW78', a tightly upright columnar form and female flowers were observed. *Acer rubrum* 'Red Rocket' (unpatented) was also very tightly upright in form and produced bright red fall colors, but was slower growing than most desirable for commercial nursery production and landscape use. Importantly, 'Red Rocket' produced male flowers. To combine the best characteristics of 'JFS-KW78' and 'Red Rocket', they were hybridized in the spring of 2005.

The hybridization was successful, seed was produced and germinated, and five seedling trees were grown. These seedling trees were transplanted into a nursery row in Boring, Oregon and grown for one season. Four of these trees were promising in form and were transplanted in 2008 into an evaluation row, while the fifth tree was destroyed. After observing and evaluating these four trees in 2008 and 2009, the best two trees were kept and transplanted into a long term evaluation block, and the remaining two trees were destroyed. Of these two remaining sibling trees, the superior tree was given the cultivar name 'WW Warren' and the other tree was destroyed in 2020 as inferior in form and appearance.

Beginning in 2013, small plots of 'WW Warren' were propagated by budding onto *Acer rubrum* rootstock and grown in nursery rows in Boring, Oregon. Small trial plots continued to be propagated in the same nursery through 2019. A total of 75 nursery row trees were grown and evaluated. Of these, all were destroyed after evaluation except for 10 trees that were kept as stock trees for eventual commercial propagation and planted in the same Boring, Oregon nursery in 2020.

'WW Warren' was observed and evaluated in the long term evaluation block from 2010 through 2023 as were the propagated trees in the nursery rows. The new tree 'WW Warren' developed an excellent narrow columnar form, was fast growing, and reliably developed an attractive red fall color. From observations of the original tree and propagated trees, it was determined that the characteristics of 'WW Warren' were firmly fixed in successive generations and had unique and valuable characteristics for nursery production, landscape use, and street plantings.

SUMMARY

This new cultivar possesses a unique combination of characteristics in that it combines a fast growth rate with tightly upright fastigiate branching with a narrow columnar form. The medium green foliage turns each fall into a reliable display of bright red fall color.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
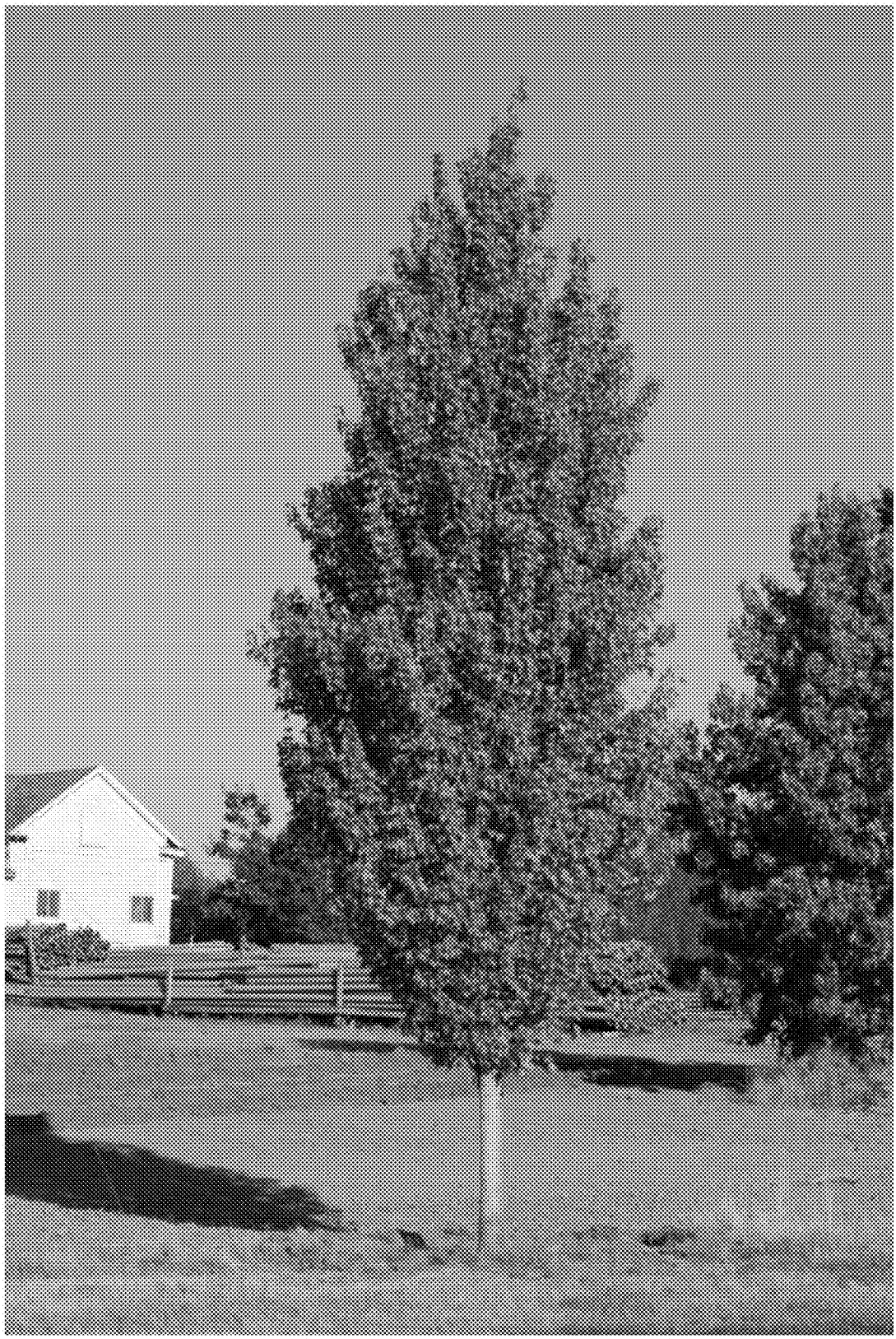
FIG. 1: Illustrates the original tree at 18 years of age in summer foliage, showing its columnar to narrow shape.
Figure 2:
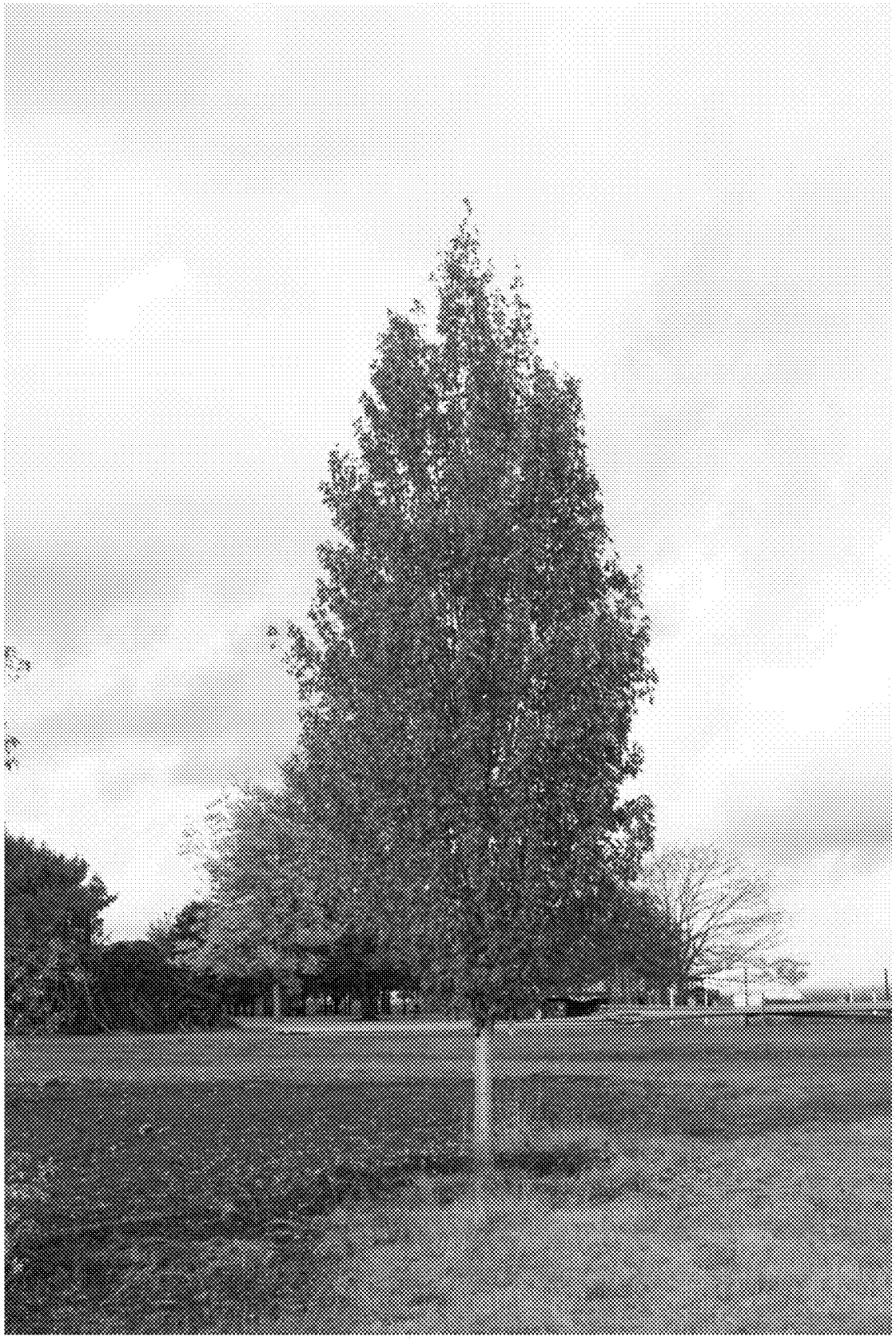
FIG. 2: Illustrates the original tree at 18 years of age in fall color, illustrating the brightness red fall color and the tightly upright shape.
Figure 3:
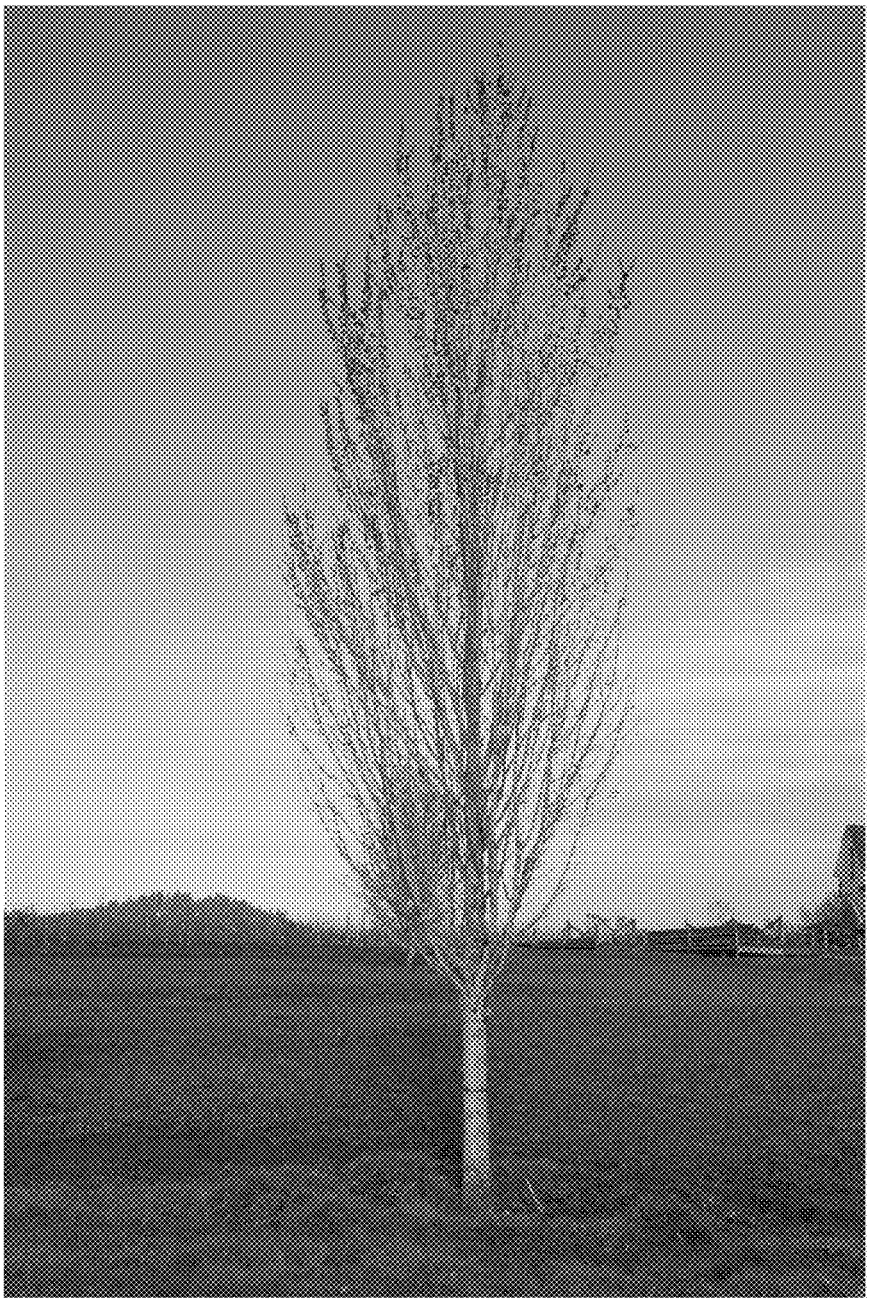
FIG. 3: Illustrates the original tree at 16 years of age in after defoliation, showing its columnar to narrow shape.
Figure 4:
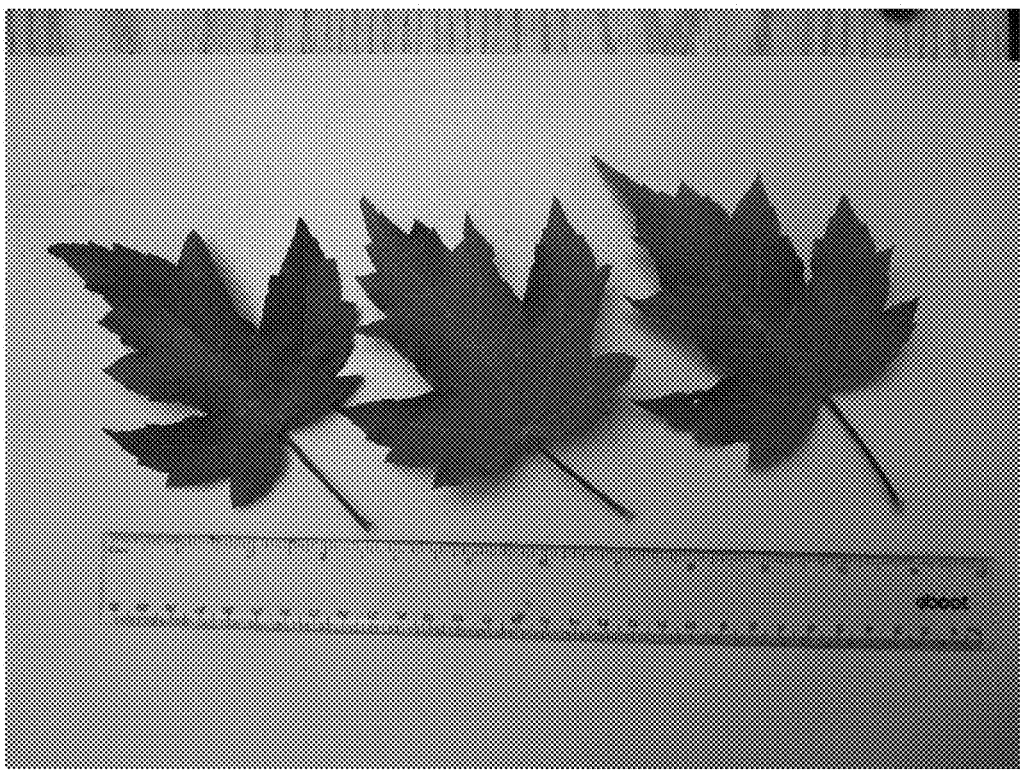
FIG. 4: A close up of the top surface of the leaves on a grey board with scale showing size and summer color.
Figure 5:
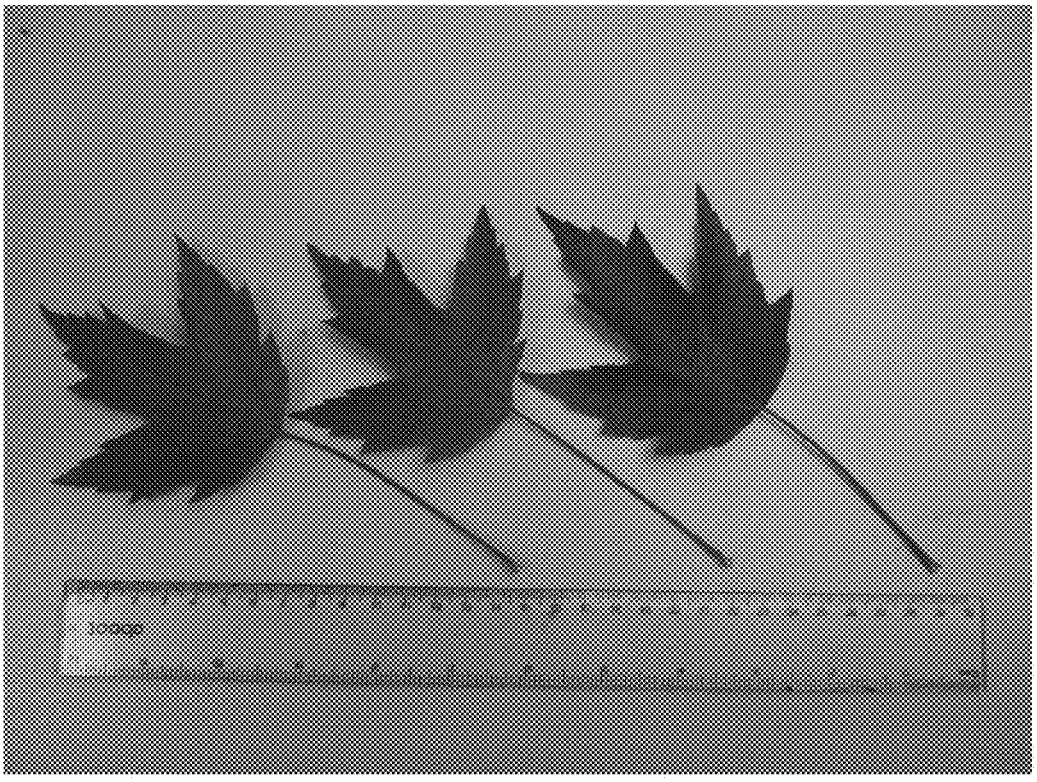
FIG. 5: A close up of the top surface of the leaves on a grey board with scale showing size and fall color.
Figure 6:
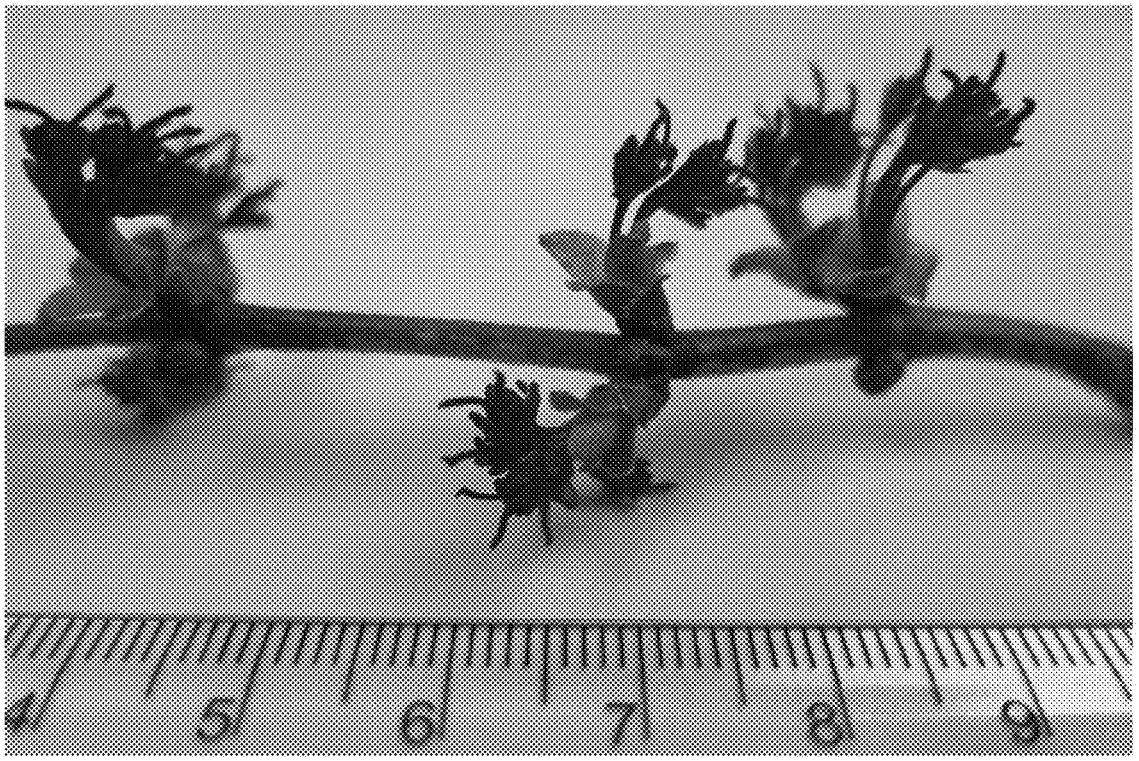
FIG. 6: A close-up of the pistilate flowers on a grey board with scale showing size and colors.
Figure 7:
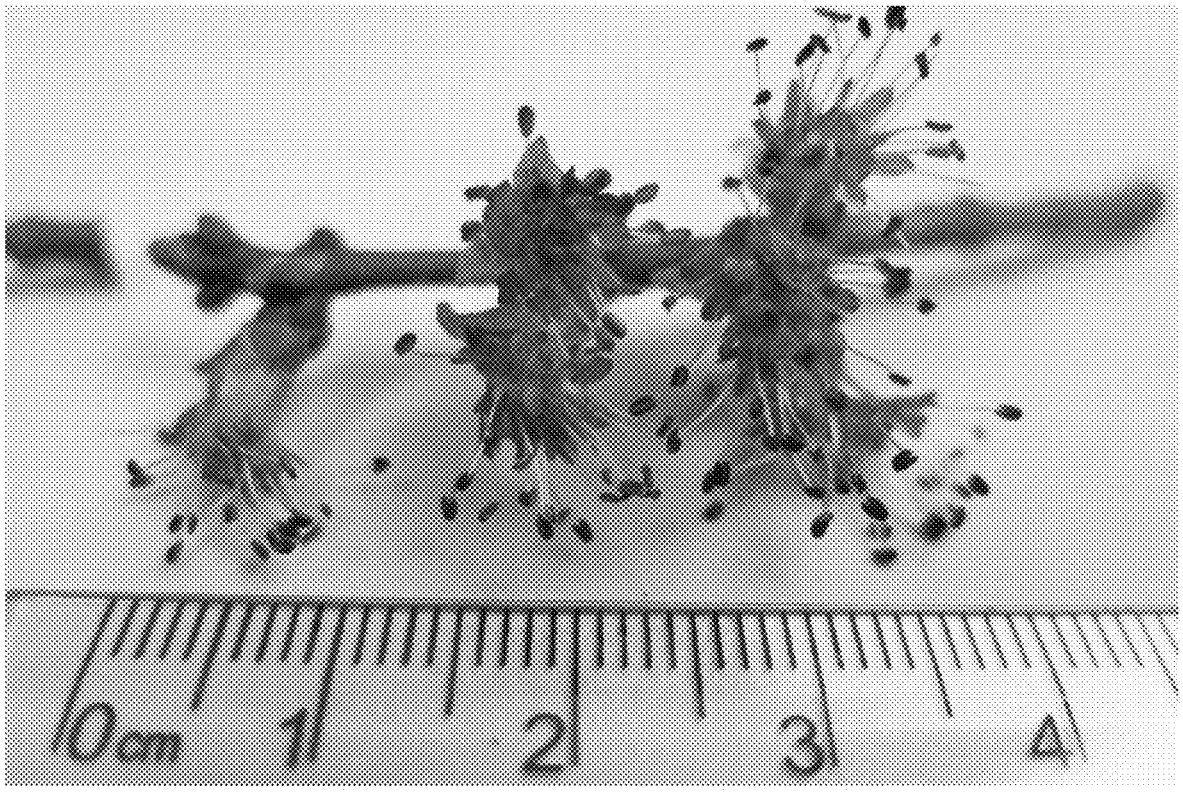
FIG. 7: A close-up of the staminate flowers on a grey board with scale showing size and colors.
Figure 8:
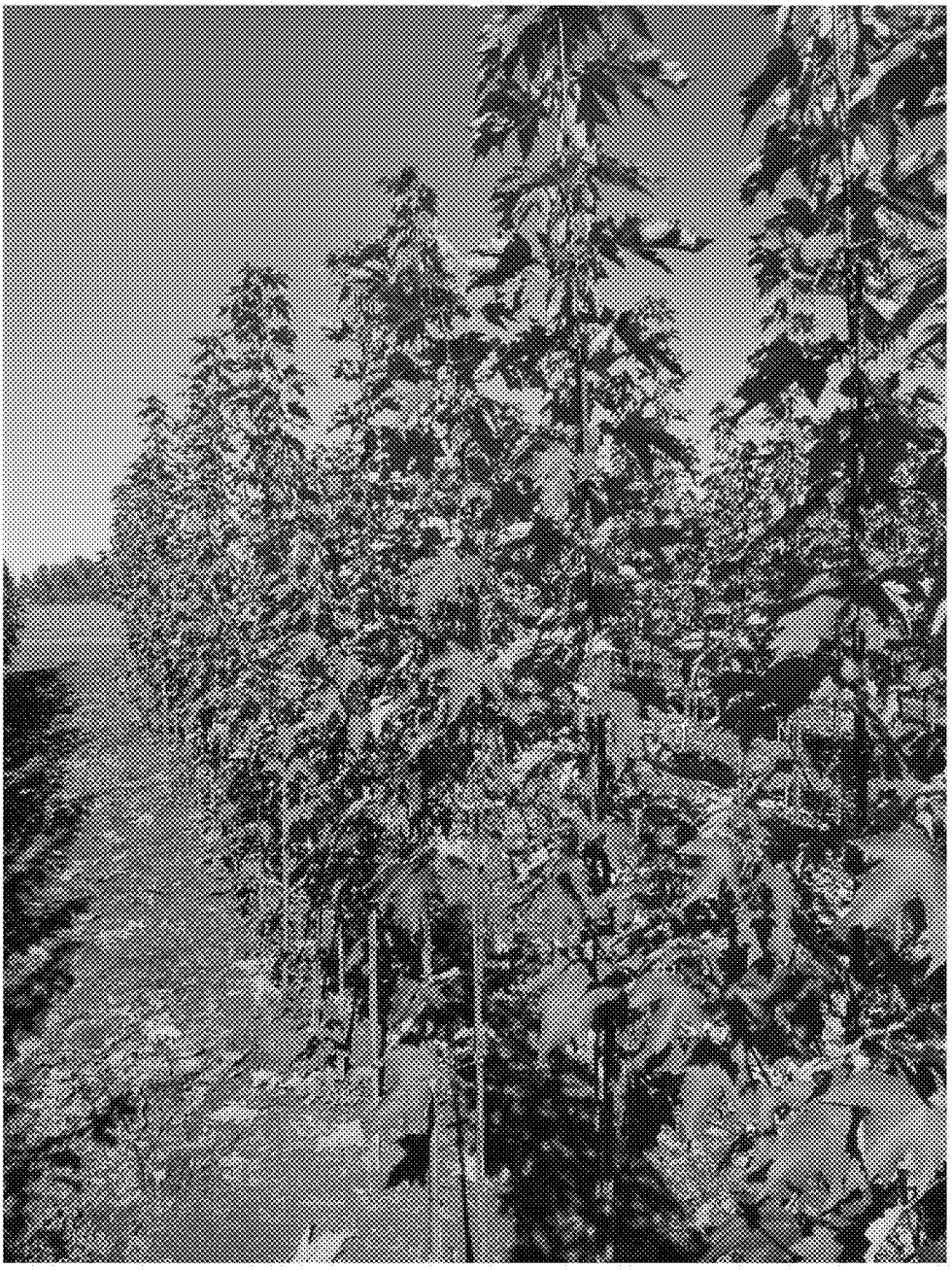
FIG. 8: Illustrates 1 year old trees growing in a nursery row in Boring, Oregon in late summer.
Figure 9:
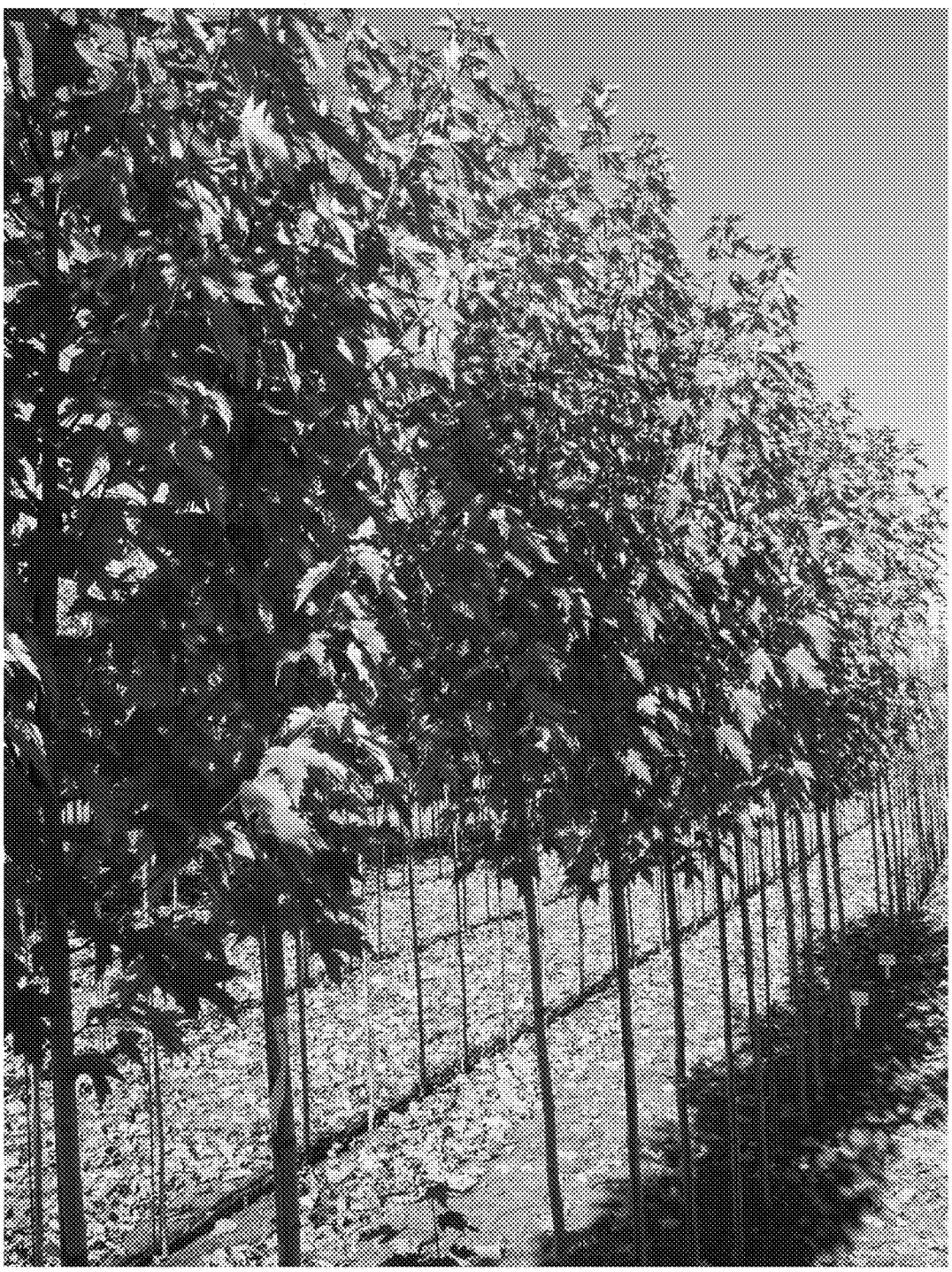
FIG. 9: Illustrates 2 year old trees growing in a nursery row in Boring, Oregon in October showing typical fall color.

The following detailed description of the 'WW Warren' variety is based on observations of the original tree and one, two, and three year old progeny. The observed progeny were trees which were growing in Boring, OR.

The following is a detailed description of my new red maple tree with color descriptions using terminology in accordance with The Royal Horticultural Society (London) Colour Chart©, 1986.

Scientific name: *Acer rubrum* 'WW Warren'.

Parentage:

*Seed parent.*—*Acer rubrum* 'JFS-KW78'.

*Pollen parent.*—*Acer rubrum* 'Red Rocket'.

Tree:

*Overall shape.*—A tightly fastigiated branching habit, the tree develops a dense, upright, narrow, columnar shape.

*Height.*—11.5 meters at 19 years of age.

*Width.*—2.5 meters at 19 years of age.

*Growth rate.*—Fast when compared to other cultivars of *Acer rubrum.*

*Diameter.*—18.7 cm at 10 cm height, 16.5 cm at 1 meter, at 19 years of age.

*Trunk.*—Straight, strongly upright, single stem with a very gradual taper.

*Trunk bark texture.*—Smooth on 1 and 2 year old trees. Smooth on original tree at 19 years of age.

*Trunk bark color.*—

*Immature bark color on* 1 *year old trees.*—Any color between Greyed-Orange 163B and Greyed-Orange 164B (endpoints included) measured at 1 meter height in September.

*Immature bark color on* 2 *year old trees.*—Any color between Greyed-Orange 164A and Greyed-Orange 166B (endpoints included) measured at 1 meter height in September.

*Mature bark color.*—Any color between Grey-Green 197A and Grey-Green 198B (endpoints included) without striations.

*Trunk lenticels.*—Not visible on trunk of original tree at 19 years of age.

*Primary branches.*—On the original tree at 19 years of age: strongly fastigiate and ascending, curving upward to a vertical orientation from crotch angles that are generally 30° to 50°. Longest primary branches on the original tree at 19 years of age are 3 to 4 meters long. On two year old trees in a nursery in Boring, OR, branches are tightly upright producing a very narrow form.

*Branch color.*—Young branches, during their first season of growth, are smooth barked, Greyed-Orange 171A and Grey-Brown 197A as they mature in the fall. They become Greyed-Orange 173A and Greyed-Orange 164A in the winter. During their second season, branches are anywhere between Greyed-Orange 164A and Greyed Orange-165B (endpoints included) as they mature in the fall then become Greyed-Orange 177C and Grey-Brown 199A in the winter.

*Branch lenticels.*—On branches of trees of 2 years of age: broadly oval to oblong, typically 1 to 2 mm long by 0.5 mm to 1.0 mm wide. Color is Yellow-White 158A.

*Dormant buds.*—Ovoid with acute to obtuse tip, with imbricate scales, very slightly appressed against the twig, 2 mm to 4 mm long by 1 mm to 2 mm in diameter, Greyed-Orange 176A and Greyed-Purple 182B.

*Bud break.*—Bud break averages April 10-15 under Boring, OR conditions. Bud break is a little later than average for the species.

*Internodes.*—Average length is 8.9 cm when measured on the mature branches of 2 year trees.

*Hardiness.*—Has tolerated field temperatures to 10 degrees F. without damage in Boring, OR and Canby, OR. It is believed to have Zone 4 cold hardiness similar to other plants of this species.

*Disease and insect resistance.*—Appears similar to the species with no differences noted.

Leaves: Except as otherwise noted, observations are from twenty vigorous growth leaves on trees grown in a nursery in Boring, OR.

*Arrangement.*—Opposite.

*Type.*—Simple.

*Texture.*—Smooth on upper surface. Slightly wrinkled by veins on lower surface.

*Sheen.*—Dull on upper surface. Dull on lower surface.

*Length.*—7 to 18 cm. on 1 and 2 year old trees (leaf blade, excluding petiole).

*Width.*—7 to 15 cm. on 1 and 2 year old trees (leaf blade, excluding petiole).

*Petioles.*—5 cm to 9 cm long×1 mm to 2 mm in diameter when measured on one and two year old trees. Color on the upper surface where exposed to sunlight is Orange Red 34A. Where petiole is in shade, color of upper surface will vary to Yellow-Green 144B. Lower surface of petiole is Yellow-Green 145C.

*Overall shape.*—Palmate with three main lobes, and six to eight minor lobes. Lobe tips are acuminate. The longest lobe is central and is typically 50% to 60% of the length of the leaf blade. The longest two side lobes are typically 30% to 40% of the length of the leaf blade.

*Margin.*—Irregularly coarsely serrate.

*Tip.*—Long acuminate.

*Base*.—Cordate to truncate to broadly acute. Leaves on young trees generally have cordate to truncate bases, while leaves on trees older than three years have leaves tend to be more broadly acute.

*Stipules*.—None.

*Spring leaf color*.—Any color between Yellow Green 144C and 145A (endpoints included). Lower surface is 145B and 149D.

*Summer leaf color*.—

*Upper leaf surface*.—Any color between Green 137A and Yellow-Green 139A (endpoints included).

*Lower leaf surface*.—Green 139C and 139D.

*Vein*.—Yellow-Green 144B.

*Appearance*.—Foliage remains fresh and attractive all Summer.

*Fall leaf color*.—Individual leaves can be any color between Red 45A and Red 47A (endpoints included) on top surface, and lower surface can be any color between Red 43B and Red 44C (endpoints included). From a distance, the overall color of the tree with foliage in mass appears similar to Red 45A.

*Timing of fall leaf color*.—Average dates for original tree in Boring, OR.

*Onset*.—October 10.

*Peak*.—October 25.

*Latest extent of fall color*.—November 5.

*Defoliation*.—After peak fall color, the tree gradually loses the brightness of its fall color and defoliation begins. In Boring, OR, the original tree is typically 50% defoliated by the end of October, and completely defoliated by November 5th.

*Persistence*.—The tree is deciduous.

Flowers:

*Overall*.—A small nearly sessile to short stalked umbel of generally three to five flowers. Flowers are held tightly at first opening and are surrounded by four bud scales. The pedicels gradually elongate as flowers mature. The tree produces predominately pistilate (female) flowers. Some branches also produce staminate (male) flowers.

Pistilate flowers:

*Shape*.—Individual flowers are urn shaped at the base, slightly flattened in one dimension, with stigmas flaring outward from the styles.

*Size*.—Individual flowers are 6 mm wide×9 mm tall.

*Flower buds*.—2 mm to 3 mm wide x 3-5 mm long, ovoid.

*Color*.—

*Unopened buds*.—Any color between Greyed-purple 183A and Greyed-Purple 184B (endpoints included).

*Opened flower*.—The overall flower cluster appears Red 46A, surrounded by bracts that are any color between Red 45A and Red 47A (endpoints included).

*Petals and sepals*.—Reduced to a series of four each, very similar in appearance. Petals are oblong-obovate, 2 mm long×1 mm wide, have a smooth margin, and are Red 42B on both surfaces. Petal tip is irregularly rounded. Sepals are oblong-obovate, 2 mm long×1 mm wide, have a smooth margin, with a color gradation on both surfaces from mostly Greyed-Yellow 162A in the center to Greyed-Red 178A on edges. Sepal tip broadly acute of irregularly rounded.

*Stamens*.—Nonfunctional. Reduced to a series of generally five, inside of petals and sepals. 1 mm high× 0.5 mm wide. Stamens do not elongate beyond the corolla.

*Pistil*.—A single pistil with two carpels. Style is short, 1 mm. The style divides near the base into two elongated, exerted stigmas, each 3 mm to 4 mm long×0.5 mm in diameter, velvety texture, Red 53A.

*Pedicel*.—

*Length*.—1 mm at the onset of flowering, extending up to 12 mm at the end of flowering.

*Diameter*.—0.5 mm.

*Color*.—Red 46B.

*Surface texture*.—Smooth.

*Pubescence*.—Flowers are glabrous, stigmas are velvety and flower bud scales which are finely tomentose at the margins.

*Fragrance*.—None.

Staminate flowers: Flowers are not stalked and emerge from buds on the branch tips.

*Opened flower*.—The overall flower cluster appears Red Purple 60A.

*Pedicel*.—1-2 mm long, Red Purple 67A.

*Sepals*.—2 mm long×1 mm wide, Red Purple 60C.

*Stamens*.—Generally 4-8 per flower.

*Filaments*.—5 mm-9 mm long, Red Purple 69A.

*Anthers*.—1 mm long×0.5 mm wide, Brown 200C.

*Pollen*.—Yellow 11A.

*Flowering date*.—Based on 2023 data for the original tree in Boring, Oregon.

*First bloom*.—March 20.

*Peak bloom*.—March 26.

*End of bloom*.—April 4.

Fruit: Observations are from a sampling of typical fruit. The fruit is a samara, held in pairs by a pedicel in clusters of up to 3-5. The samara is attached at the seed end and the wings diverge at a 25 to 30 degree angle. The samaras are striated with a papery wing.

*Size*.—25-30 mm x 10 mm×3 mm thick at seed end.

*Shape*.—Asymmetrically elongated with wing which becomes papery thin.

*Lenticels*.—None

*Color*.—When first formed, samaras are any color between Yellow-Green 151A and Yellow-Green 153A (endpoints included). As they ripen, they turn to anywhere between Greyed-Orange 179A and Greyed-Orange 180A (endpoints included).

*Seeds*.—Oval, 5 mm×4 mm×2 mm thick, slightly pointed at the attachment end. Any color between Greyed-orange 166D and Greyed-Orange 167A (endpoints included).

*Fruit production*.—The trees produced some fruit every year depending on conditions fruit set can be light to moderate.

*Fruit maturity*.—Based on 2022 data, fruit matures and drops from tree May 15 to May 30.

*Usage*.—None.

COMPARISON TO THE SPECIES

'WW Warren' has a strongly fastigiate branch habit that develops a canopy that is tightly columnar to narrow. Branches curve upward close to the main trunk becoming nearly vertical and parallel. Typical seedlings of the species have upright spreading branches and canopies that develop into a broadly oval to rounded shape.

Data in the following tables was all collected from trees growing in a nursery in Boring, Oregon.

TABLE 1

| Feature: | 'WW Warren' | Seedling *A. rubrum* |
|---|---|---|
| Crotch angle, mid canopy branches | 65° to 85° | 45° to 80° |
| Crotch angle, canopy base | 75° to 90° | 60° to 90° |
| Branch angle degrees from vertical, 50 cm proximal to tip of mid-canopy branches | 25° to 35° | 40° to 80° |
| Leaf blade size, average of 1 year tree in mid-canopy | 15.0 cm long × 12.5 cm wide | 15.8 cm long × 16.3 cm wide |
| Leaf tip narrowness, expressed as distance from tip to the point at which the central tip lobe is 1 cm wide, average | 2.1 cm | 1.6 cm |

COMPARISON TO THE SEED PARENT

My new tree can be most noticeably distinguished from its seed parent, *Acer rubrum* 'JFS-KW78', by its excellent red fall color and the fact that it has both pistilate & staminate flowers. These and other differences are listed in Table 2.

TABLE 2

| Feature: | 'WW Warren' | 'JFS-KW78' |
|---|---|---|
| Bud break time, comparative | Late | Late |
| Growth rate | Fast | Moderate |
| Height of 1 year trees, average | 220 cm | 188 cm |
| Height of 2 yr trees, average | 3.5 m | 3.23 m |
| Branch length, 1 year tree, average at 1 meter height | 24 cm | 18 cm |
| Branch length, 2 year tree, average of top four branches | 1.35 m | 1.13 m |
| Branch angle degrees from vertical, 50 cm proximal to tip of mid-canopy branches of 2 year trees | 15° to 30° | 10° to 30° |
| Trunk diameter, 2 year tree, average at 10 cm height | 2.8 cm | 2.7 cm |
| Leaf blade size, average of 1 year tree in mid-canopy | 13.8 cm long × 12.2 cm wide | 11.8 cm long × 11.1 cm wide |
| Fall Color | Red 45A | Orange-Red 30B |
| Flowers | Pistilate & Staminate | Pistilate Only |

COMPARISON TO THE POLLEN PARENT

TABLE 3

| Feature: | 'WW Warren' | 'Red Rocket' |
|---|---|---|
| Growth rate | Fast | Slow |
| Height of 1 year trees, average | 220 cm | 165 cm |
| Height of 2 yr trees, average | 3.5 m | 3.00 m |
| Trunk diameter, 2 year tree, average at 10 cm height | 2.8 cm | 2.6 cm |

COMPARISON TO MOST SIMILAR OTHER CULTIVATED VARIETIES

'WW Warren' can easily be distinguished from most other cultivars of *Acer rubrum* by its tightly fastigiate, narrow form. In addition to 'JFS-KW78', the seed parent of my new tree, there are four upright growing *Acer rubrum* cultivars that are somewhat similar to 'JFS-KW78'.

TABLE 4

| Feature: | 'WW Warren' | 'Red Rocket' (not patented) | 'Scarlet Sentinel' (not patented) | 'Karpick' (not patented) | 'Bowhall' (not patented) |
|---|---|---|---|---|---|
| Bud break time, comparative | Late | Middle | Early | Middle | Very early |
| Mature tree shape | Tightly fastigiate, columnar to extremely narrow | Upright narrow to narrow oval | Upright narrow oval to oval | Upright ovate to broadly pyramidal | Tightly fastigiate, narrow |
| Leaf tip | Long acuminate | Acute to acuminate | Acute to acuminate | Acuminate to long acuminate | Acute to acuminate |

I claim:

1. A new and distinct variety of red maple tree named 'WW Warren'. substantially as illustrated and described herein.

* * * * *